United States Patent [19]

Reul

[11] 4,291,420
[45] Sep. 29, 1981

[54] ARTIFICIAL HEART VALVE

[75] Inventor: Helmut Reul, Duren, Fed. Rep. of Germany

[73] Assignee: Medac Gesellschaft fur Klinische Spezialpraparate mbH, Hamburg, Fed. Rep. of Germany

[21] Appl. No.: 159,386

[22] Filed: Jun. 13, 1980

Related U.S. Application Data

[63] Continuation of Ser. No. 33,942, Apr. 27, 1979, abandoned, which is a continuation of Ser. No. 655,373, Feb. 5, 1976, abandoned, which is a continuation of Ser. No. 463,135, Apr. 22, 1974, abandoned.

[30] Foreign Application Priority Data

Nov. 9, 1973 [DE] Fed. Rep. of Germany ....... 2355959

[51] Int. Cl.³ .............................................. A61F 1/22
[52] U.S. Cl. ........................................ 3/1.5; 137/846; 137/853
[58] Field of Search ................ 3/1.5, 1; 137/846, 849, 137/853

[56] References Cited

U.S. PATENT DOCUMENTS

| | | | |
|---|---|---|---|
| 3,197,788 | 8/1965 | Segger | 3/1.5 |
| 3,736,598 | 6/1973 | Bellhouse et al. | 3/1.5 |
| 3,744,062 | 7/1973 | Parsonnet | 3/1.5 |

FOREIGN PATENT DOCUMENTS 158988 5/1964 U.S.S.R. .................................. 3/1.5

OTHER PUBLICATIONS

"The Direct Approach for Correction of Aortic Insufficiency" by Charles A. Hufnagel et al., Journal of American Medical Assoc., vol. 178, No. 3, Oct. 21, 1961, pp. 275-279.

"Herzklappenprosthesen" by Von W. Seidel, *Deutsche Medizinische Wochenschrift*, 88, Nr. 15, Apr. 12, 1963, pp. 748-754.

"Comparable Study of Cardiac and Vascular Implants in Relation to Thrombosis" by C. A. Hufnagel et al., *Surgery*, vol. 61, No. 1, pp. 11-16, Jan. 1967.

*Primary Examiner*—Ronald L. Frinks
*Attorney, Agent, or Firm*—Cushman, Darby and Cushman

[57] ABSTRACT

An artificial, triple-lobed semilunar valve is disclosed for replacing the aortic or pulmonary valve in the heart. The valve includes a flexible suture ring which conforms to the shape of the aortic root and three flexible pockets which are mounted within the suture ring. When fluid flows through the suture ring in one direction, the pockets bend outwards to the vessel wall and lie free-floating in the fluid, thereby permitting fluid to flow through the valve. However, when the fluid begins to flow in the opposite direction, the pockets open and contact one another to close the valve thereby preventing fluid flow in the opposite direction.

9 Claims, 6 Drawing Figures

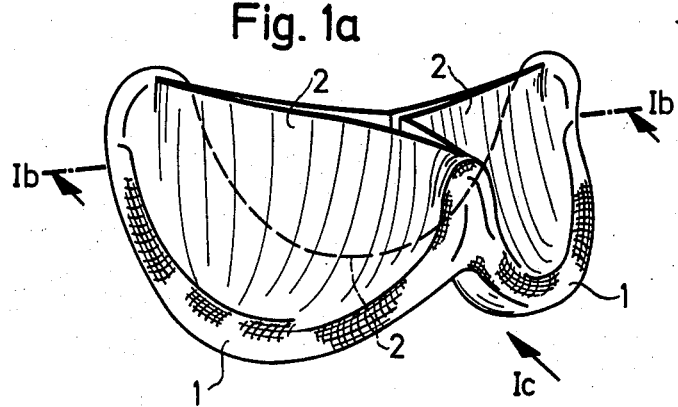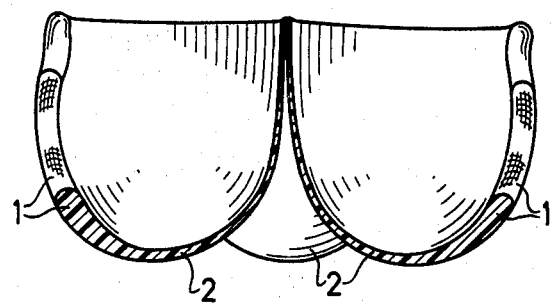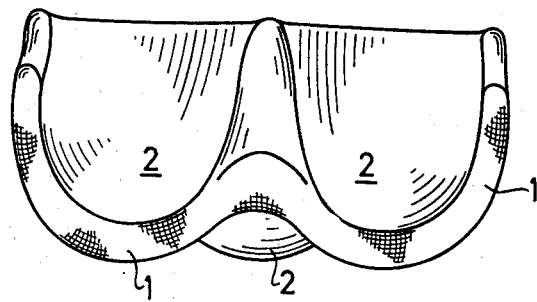

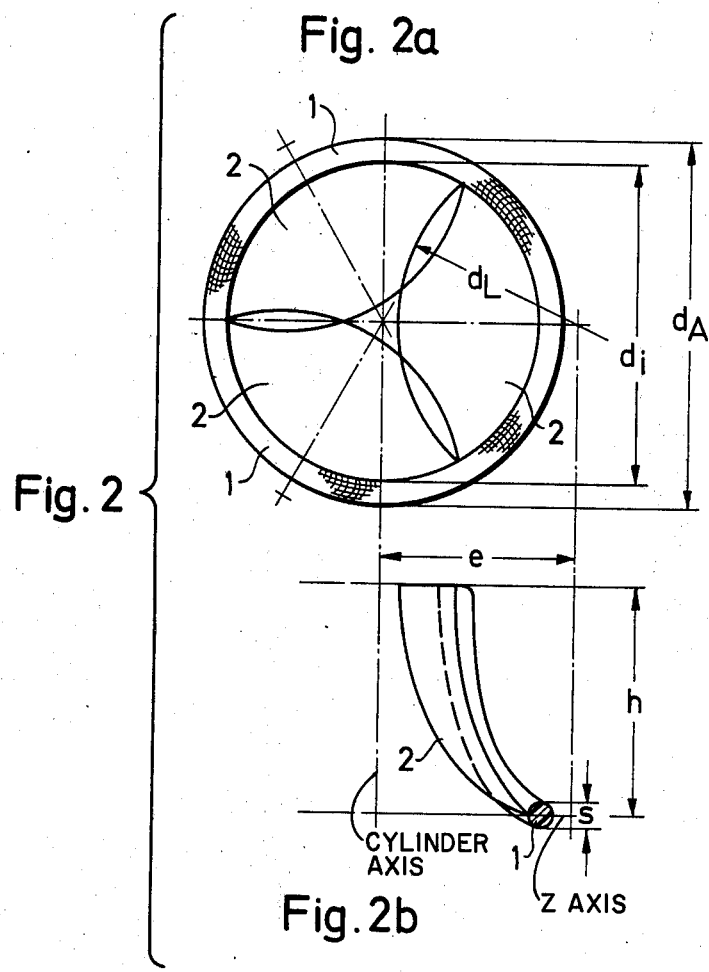

ARTIFICIAL HEART VALVE

This is a continuation of application Ser. No. 33,942 filed Apr. 27, 1979, which in turn is a continuation of Ser. No. 655,373, filed Feb. 5, 1976, which in turn is a continuation of Ser. No. 463,135, filed Apr. 22, 1974, which are now abandoned.

BACKGROUND OF THE INVENTION

This invention relates to an artificial heart valve. More specifically, this invention relates to a flexible, artificial, triple-lobed semilunar or pocketed valve intended for use in surgery to replace the natural aortic or pulmonary valve in the heart. While the valve of this invention is primarily intended for use in the human heart, it may also be of use in the hearts of animals.

For about twenty years it has been possible, in cases of heart valve inadequacy or heart valve stenosis, to replace the damaged natural heart valves by prostheses. This technique is primarily used for the replacement of all four heart-valves. Most of the prostheses developed for this purpose were ball valves or disk valves, and such valves are still predominantly being used today. These prostheses correspond to the check valves that are customarily used in technical applications. A freely movable ball or disk is disposed over an inflexible aperture which is usually circular and the ball or disk is held within a cage. When the liquid flows in the desired direction, the ball or disc lifts off from the flow aperture in the desired direction or opens through a specified angle and thus opens the outlet channel for the passage of blood. However, when the fluid flow is in the opposite direction, the ball or disk seats itself in front of the aperture and thus prevents a back flow of the blood. When used as a replacement for the natural cardiac semilunar valves, these valves have proven to operate reliably as check valves. However, a marked disadvantage is that the ball or the disk is located in the blood stream, thereby requiring lateral flow of the blood around the ball or disk thereby presenting a considerable flow resistance or drag. In comparison with the natural semilunar valve in which the flow is central, the lateral flow caused by the ball or disk leads to a substantially higher pressure drop across the valve.

For this reason, attempts have been made to develop heart valve prostheses which resemble the natural semilunar cardiac valves and, hence, offer a lower resistance to the blood flow. See, for example, D. B. Roe et al, Circulation 33, 124, (1966), Supplement I; Charles A. Hufnagel, Annals of Surgery 167, 791-95 (1968). However, these prostheses have not been fully successful in clinical practice, primarily because their closure reliability is lower than that of the customary ball valves and disk valves.

Most previously known prostheses for the replacement of heart valves have the common disadvantage of having a rigid basic structure. In the case of ball valves and disk valves, this is inherent in their construction because reliable closure requires the valve seat to have a constant shape. Even in the previously known artificial semilunar valves, the suture rings are made rigid by a metal insert so that they cannot adjust to the natural changes in size of the aorta which surrounds them after the implantation. Bellhouse, et al. disclosed in U.S. Pat. No. 3,736,598 a flexible cardiac valve having a suture ring which consists of an annular ring with three, equiangularly spaced projecting legs which extended substantially parallel to one another in the axial direction of the ring. The suture ring supports three, separate cusps. This suture ring, however, has a ring portion at the bottom thereof which interconnects the bottom portions of the projecting legs thereby preventing free, radial movement of the bottom portions with the expansion of the aortic root.

To overcome these disadvantages, the present invention seeks to develop a completely flexible artificial heart valve which has as low a flow resistance as possible but which, at the same time, operates completely reliably over long periods of time.

STATEMENT OF THE INVENTION

Accordingly the present invention relates to an artificial, triple-lobed semilunar valve for the replacement of the aortic or pulmonary valve in the heart. The valve includes three flexible pockets mounted within a suture ring, each pocket being displaced from the other by 120°, with the shape of the suture ring corresponding to the natural aortic root. The suture ring is formed of three, U-shaped legs which are joined to one another at the top portions thereof and are left free at the bottom portions thereof so that the bottom portions can freely move with respect to one another, particularly in the radial direction. Thus, the suture ring can freely expand and contract with the natural dilation and contraction of the aortic root. The individual pockets are made to overlap so that they have surface-to-surface contact in the closed position. Thus, when blood flows through the suture ring in one direction, the pockets bend outwards to the vessel wall and lie free-floating in the fluid, thereby permitting fluid to flow in this direction through the suture ring. However, when the fluid attempts to flow in the opposite direction through the suture ring, the pockets open and make contact with one another, thereby occluding the aperture within the suture ring to thereby prevent fluid flow in the opposite direction. Preferably, the suture ring is also made flexible so as not to impede the movement of the aortic wall.

Because of the design of the individual pockets according to the invention, the valve closure occurs rapidly and the individual pockets close tightly, thereby making surface-to-surface contact with one another so that the valve operates properly. The pockets each have a certain amount of reserve surface area which guarantees good closure and static support between the individual pockets so that a "break-through" of the back flow is practically impossible. The stresses occurring in the valve are distributed not only on the insertion edge but over the entire closure edge of the valve, thereby avoiding localized stress peaks.

The construction of the valve according to the invention guarantees laminar flow of the blood through the open semilunar valve without the presence of any disturbing elements whatsoever lying in the blood stream, thereby obviating the problems inherent with the ball or disk valve. Therefore, the flow losses due to the valve are unusually low and differ only slightly from those in the healthy human heart.

The completely flexible construction of the novel semilunar valve of the present invention is particularly esential. The contraction of the ventricular outlet channel occurs progressively from the tip of the heart to the aorta with shortening of the outlet channel and enlarging of the aortic root. During systole, the aortic root is stretched until the valve edges are stretched. Further reduction in size occurs by means of the sub-aortic annular musculature of the left expulsion or outflow channel and because of the pressure-dependent relaxation of the aorta. This systolic enlargement of the aortic root also effects the closure of the mitral valve. Thus, whereas the mitral ostium is nearly circular during diastole, it becomes elliptical during systole with the two commissures lying on the major axis of the ellipse. The occurrence of the elliptic deformation of the mitral ostium is due to the transmission of the pulsations of the aortic root to the neighboring insertion region of the mitral flap. Thus, the aortic flap approaches the mural flap and the flap area is enlarged with respect to the area of the ostium. This results in an improvement of the closure capability which is also guaranteed even if the mitral ostium is enlarged. Stereophotographic measurements under various conditions of loads have shown, furthermore, that the largest dilations occur in the region of the coronary outlets.

This natural distribution of the volumetric elasticity is as technically expected, since the closer a surge tank is placed to the beginning of a conduit system having pulsating fluid flow, the more effective is the reduction of pressure peaks. It is, however, exactly in this region of maximum dilation that the suture rings of conventional aortic valves are fixed. Hence, when employing a rigid suture ring, such as is present in all previously known prostheses, all dilation is prevented, and, in the course of time the previously described functional cooperation of the whole valve-heart-aorta systems is affected and this can cause disturbances to the heart.

The semilunar valve according to the invention is the first valve to overcome this problem because even its suture ring is made completely flexible. Thus, in the relaxed position, the shape of the suture ring conforms to that of the natural valve edges on the inside wall of the aorta, i.e., the ring has the form of a "triple-lobed" circle, bent downwardly in the region of the individual pockets. By straightening these bowed regions, the suture ring is capable of considerably enlarging its diameter and can, therefore, adjust to the diameter changes of the aorta. In this manner, the aortic root substantially retains its natural capacity for changing its diameter. The blood flow is also substantially improved by the flexible construction of the semilunar valves. Because of the constant motion of all parts of the valve, the creation of regions of unmoving blood is markedly reduced and hence risk of thrombosis occurring is substantially reduced.

BRIEF DESCRIPTION OF THE DRAWINGS

Other objects, features and advantages of the present invention will be more fully apparent from the following detailed description, appended claims and the accompanying drawings in which:

FIG. 1a is a perspective view of the semilunar valve according to the invention;

FIG. 1b is a section view taken along the line $I_b$—$I_b$ of FIG. 1a;

FIG. 1c is an elevation view of the valve according to the invention looking in the direction of Arrow 1c of FIG. 1a;

FIG. 2a is a schematic representation of the construction of the semilunar valve according to the invention showing the theoretical overlap of the upper rim of the pockets; and FIG. 2b shows a section through one pocket in the plane of the cylinder axis and the Z-axis of the ellipsoid;

DETAILED DESCRIPTION OF THE PREFERRED EMBODIMENT

Figure 3:
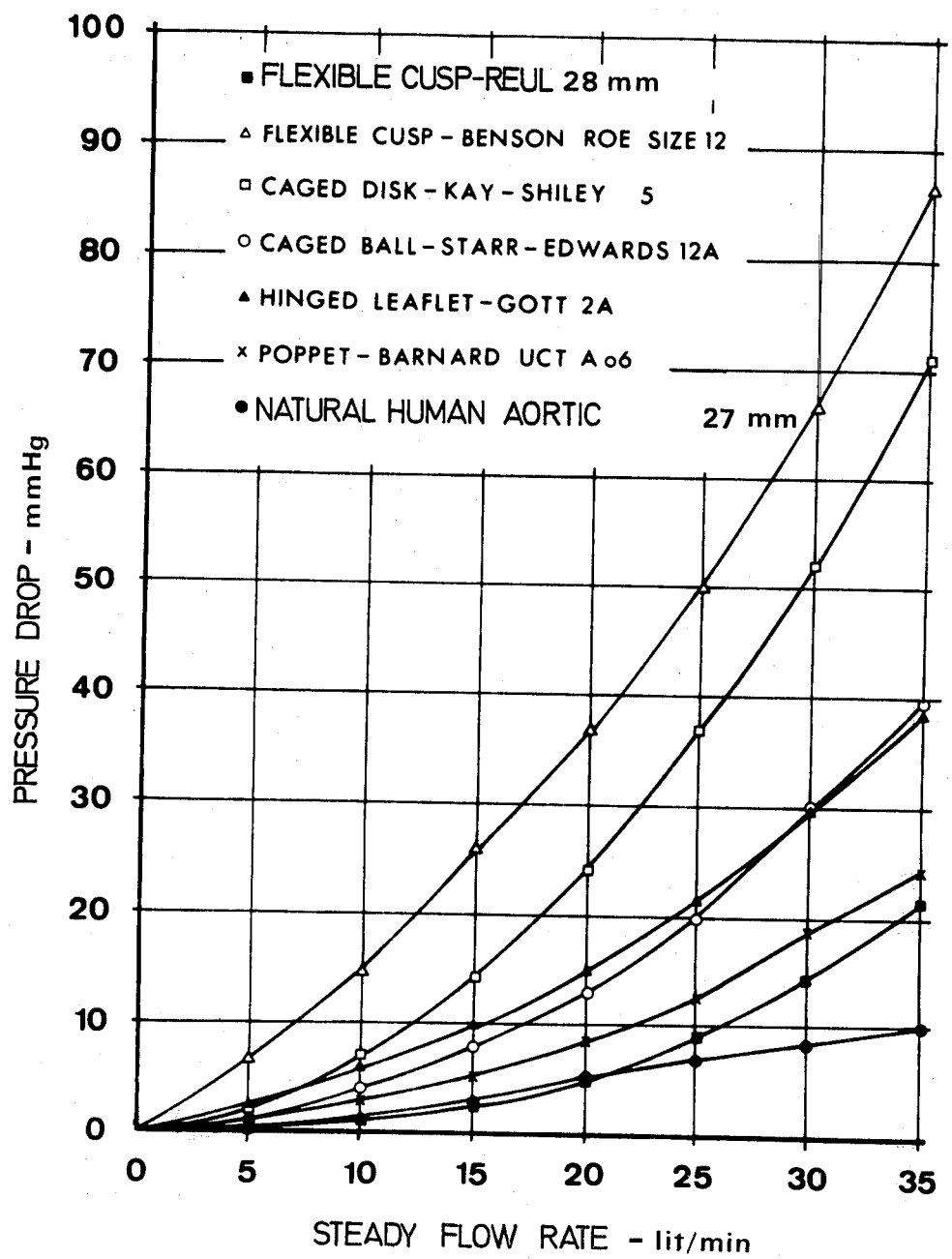
FIG. 3 is a comparative graphical representation of the pressure drop across different valves.

The semilunar valve illustrated in FIGS. 1 and 2 includes a suture ring 1 and the three pockets 2 mounted within the ring. The suture ring has three symmetrical downwardly extending bulges in order to accommodate the individual pockets. As illustrated in FIG. 1 the suture ring is formed of three, U-shaped legs which are joined to one another at the top portions thereof and are not connected to one another at the bottom portions thereof. The bottom portions are thus free to move with respect to one another, particularly in the radial direction. Because of the necessity of permitting radial movement of the suture ring, there is no annular ring interconnecting the bottom portions of the U-shaped leg portions thereof. The size of the pockets 2 is such that, in theory they overlap one another within the ring. The amount of theoretical overlap is determined by the difference of the lengths $$d_L . \pi/360 \text{ arc sin } (d_i/d_L \cos 30°) \quad (1)$$

and $$d_i/2 \quad (2)$$

where $d_L$ is the diameter of the circle, an arc of which would be described by the free edge of each pocket and $d_i$ is the internal diameter of the suture ring. In the closed position, the surfaces of the pockets do, in fact, touch each other and thereby close the valve opening which, when the pockets are not in the closed position, has the cross-sectional shape of a three-pointed star. Each individual pocket covers an angle of 120° around the inside of the ring 1. The suture ring is made flexible to permit the three downward bulges to straighten and to adjust to an increase of the aortic cross section. The shape of the individual pockets is that formed by the surface of intersection of an ellipsoid of revolution with a cylinder. The construction of the semilunar valve according to the invention is illustrated in detail by the schematic drawing of FIG. 2. In this figure $d_i$ is the inside diameter of the suture ring;

$d_A$ is the outside diameter of the suture ring which is equal to the diameter of the aorta;

$d_L$ is the diameter of each pocket, i.e., the diameter of the circle of which the edge of the pocket forms an arc;

h is the height of each pocket;

e is the eccentricity of the ellipsoid of revolution and of the cylinder; and s is the thickness of the suture ring.

Preferably, the ratio of the pocket diameter $d_L$ to the inside diameter $d_i$ of the suture ring is greater than 0.8 and smaller than 1.4, i.e., $0.8 \leq d_L/d_i \leq 1.4$ and the ratio of the pocket height h to the inside diameter $d_i$ of the sutre ring is 0.50 to 1.00, i.e.

$$0.5 \leq h/d_i \leq 1.0.$$

The following relations 3 and 4 refer to an especially preferred form of the semilunar valve according to the invention:

$$\frac{d_L}{d_i} = 1.16 \tag{3}$$

$$\frac{h}{d_i} = 0.72 \tag{4}$$

$$e = \frac{d_i}{2} \cdot \cos 60° + \frac{d_L}{2} \sqrt{1 - \left(\frac{d_i}{d_L} \cos 30°\right)^2} \tag{5}$$

$$d_A = d_i + 2^s \tag{6}$$

The equation of the ellipsoid is:

$$\frac{x^2}{\left(\frac{d_L}{2}\right)^2} + \frac{y^2}{\left(\frac{d_L}{2}\right)^2} + z^2 \frac{\left(\frac{d_L}{2}\right)^2 - \left(e - \frac{d_i}{2}\right)^2}{\left(\frac{h \cdot d_L}{2}\right)^2} = 1 \tag{7}$$

The relations 5, 6 and 7 are the basic design relations.

On the basis of these relations, the semilunar valves of this invention can be easily constructed. To allow for variations in the aortic diameter, it is necessary to manufacture the prosthesis in different sizes; in general, approximately 6 to 10 different sizes will suffice for all the human aorta diameters occurring in practice.

The semilunar valve according to the invention is manufactured from a highly flexible material having a high flexural fatigue strength and the surface is coated with a material which prevents blood coagulation. As material for the pockets, satisfactory results have, for example, been obtained using a polyester fabric (polyester fabric M S1033 made by Vereinigte Seidenwerke AG, Krefeld, Germany) coated with highly flexible silicone rubber (e.g., silicone rubber VP 3525A, made by Wacker Chemie, Munich). The suture ring for the semilunar valve can be made from a Dacron woven fabric (Dacron 6090 made by the firm duPont de Nemours, Delaware, USA).

The pressure drop which occurs when using the semilunar valve of the present invention was determined in a model experiment under conditions of steady flow and compared with the known values obtained from the literature (D. W. Wieting, Dynamic Flow Characteristics of Heart Valves, Dissertation, The University of Texas, Austin, 1969). Thus a valve having an outside diameter $d_A$ of 28 mm was cemented into a glass tube having an inside diameter of 28 mm and a length of 100 cm. The inlet and the outlet of the tube were somewhat tapered convergently but smooth transitions to the original diameter were retained. In each case, the pressure was measured at a point lying upstream and downstream from the middle of the valve. Water was passed through the pipe and the flow rate was increased from 1 liter/minute to 15 liters/minute in steps of 0.5 liter/minute. The Reynolds' numbers obtained lay between 758 and 11,400. With the aid of the Reynolds' number $Re = (w \cdot d + /\gamma)$ and of the Euler number $Eu = (\Delta p +)/(\rho w^2)$, the measured pressure gradients were converted mathematically to correspond to a fluid having a dynamic viscosity of 3.6 cp and a specific density of 1.06 g/cm³ i.e., the density and viscosity of blood.

The measurements gave the following relation between the pressure gradient $\Delta p$ and the volume of blood passing through the heart per minute (HMV).

$$\frac{\Delta p}{\text{mm H}_2\text{O}} = 0.0207 \cdot \left(\frac{HMV}{1/\min}\right)^{2.61} \tag{8}$$

The results of the measurements are graphically depicted in FIG. 3. The new flexible semilunar valve of this invention exhibits an extremely low pressure drop over the flow range investigated. Its performance, in this respect, exceeds all prostheses used for comparison and it approaches closely the values of the natural heart valve.

In conditions of pulsating flow, similarly favorable results were found for the valve of this invention. Here, also, the values of the pressure drop and of the energy loss lie within the same range of values as those for the natural heart valve.

What is claimed is:

1. An artificial, triple-lobed, semilunar valve for replacing the aortic or pulmonary valve in the heart, the valve comprising:
    a flexible, non-annular, triple-lobed suture ring having substantially no resiliency which corresponds in shape to the natural aortic root, said suture ring including three, U-shaped legs, each forming a lobe of said ring, said U-shaped legs being joined to one another at the top portions thereof and being unconnected to one another at the bottom portions thereof to thereby permit free movement of said bottom portions with respect to one another in the radial direction, said suture ring being radially expandable with the dilation of said aortic root; and
    three, flexible pockets mounted within said suture ring and disposed symmetrically at intervals of 120° to each other about the inside of said ring wherein when fluid flows in one direction through the suture ring the pockets bend outwards to the vessel wall and lie free-floating in the fluid thereby permitting said fluid to flow therethrough and wherein when said fluid begins to flow in the opposite direction through said suture ring, said pockets make surface-to-surface contact with one another thereby occluding the aperture within said suture ring and inhibiting fluid flow therethrough.

2. The semilunar valve of claim 1 wherein the surface of said pockets is coated with a material which prevents blood coagulation.

3. The semilunar valve of claim 2, wherein the suture ring has the form of a triple-lobed circle bent downwardly in the region of each of the three pockets.

4. The semilunar valve of claim 3 wherein, each pocket is formed so that, if the pocket were free to open without contacting the other pockets, the free edge of the pocket would assume the form of an arc of a cricle.

5. An artificial, triple-lobed, semilunar valve for replacing the aortic or pulmonary valve in the heart, the valve comprising:
    a flexible suture ring having substantially no resiliency which corresponds in shape to the natural aortic root; and
    three, flexible pockets mounted within said suture ring and disposed symmetrically at intervals of 120° to each other about the inside of said ring, the surface of said pockets being coated with a material which prevents blood coagulation, wherein when fluid flows in one direction through the suture ring the pockets bend outwards to the vessel wall and lie free-floating in the fluid thereby permitting said fluid to flow therethrough and wherein when said fluid begins to flow in the opposite direction through said suture ring, said pockets make surface-to-surface contact with one another thereby occluding the aperture within said suture ring and inhibiting fluid flow therethrough, said suture ring being in the form of a triple-lobed circle bent downwardly in the region of each of said three pockets, each pocket being formed so that, if the pocket were free to open without contacting the other pockets, the free edge of the pocket would assume the form of an arc of a circle, and wherein the maximum overlap of the pockets would be equal to $$\left| \left[ \frac{d_L \pi}{360} \arcsin\left( \frac{d_i}{d_L} \cos 30° \right) \right] - \frac{d_i}{2} \right|$$

where $d_L$ is the diameter of the circle an arc of which would be described by the free edge of each pocket and $d_i$ is the internal diameter of the suture ring.

6. The semilunar valve of claim 5 in which the relative sizes of the suture ring and pockets satisfy the relationship $0.8 \leq (d_L/d_i) \leq 1.4$ 7. The semilunar valve of claim 6 in which each pocket satisfies the relationship $0.50 \leq h/d_i \leq 1.00$, where h is greatest depth of each pocket.

8. The semilunar valve of claim 7 in which the shape of each pocket is such that, if free to open without contacting the other pockets, each pocket would when open assume the form of the surface generated by the intersection of an ellipsoid of rotation with a cylinder having its axis parallel with one of the axes of the ellipsoid of rotation.

9. The semilunar valve of claim 8 wherein the eccentricity e of the ellipsoid and of the cylinder is $$e = \frac{d_i}{2} \cdot \cos 60° + \frac{d_L}{2} \sqrt{1 - \left( \frac{d_i}{d_L} \cdot \cos 30° \right)^2}$$

* * * * *

UNITED STATES PATENT AND TRADEMARK OFFICE
CERTIFICATE OF CORRECTION

PATENT NO. : 4,291,420
DATED : September 29, 1981
INVENTOR(S) : REUL, Helmut

It is certified that error appears in the above-identified patent and that said Letters Patent are hereby corrected as shown below:

Column 5, Equation 5, after "$\frac{d_L}{2}$" delete --0429142001206--;

and

Equation 6, change "$d_A = d_i + 2^S$" to

--$d_A = d_i + 2s$--.

Signed and Sealed this

Sixteenth Day of February 1982

[SEAL]

Attest:

GERALD J. MOSSINGHOFF

Attesting Officer     Commissioner of Patents and Trademarks